(12) United States Patent
Bishop et al.

(10) Patent No.: US 6,979,339 B2
(45) Date of Patent: Dec. 27, 2005

(54) MEDICO-SURGICAL INSTRUMENTS

(75) Inventors: Giles Andrew Bishop, Canterbury (GB); Richard Hingley, Hythe (GB)

(73) Assignee: Smiths Group PLC, London (GB)

( * ) Notice: Subject to any disclaimer, the term of this patent is extended or adjusted under 35 U.S.C. 154(b) by 168 days.

(21) Appl. No.: 10/233,431

(22) Filed: Sep. 4, 2002

(65) Prior Publication Data
US 2003/0083672 A1 May 1, 2003

(30) Foreign Application Priority Data
Oct. 25, 2001 (GB) .................................. 0125577

(51) Int. Cl.⁷ ............................................. A61B 17/32
(52) U.S. Cl. ....................... 606/167; 606/184; 606/185; 604/264; 604/272
(58) Field of Search ............................... 606/167, 185, 606/193, 181, 184; 604/43, 44, 164, 537, 604/272, 284, 264

(56) References Cited

U.S. PATENT DOCUMENTS

| | | | |
|---|---|---|---|
| 4,073,297 A * | 2/1978 | Kopp | 604/44 |
| 4,099,528 A * | 7/1978 | Sorenson et al. | 604/44 |
| 4,217,895 A * | 8/1980 | Sagae et al. | 604/44 |
| 4,224,943 A * | 9/1980 | Johnson et al. | 604/28 |
| 4,270,535 A * | 6/1981 | Bogue et al. | 604/44 |
| 4,299,217 A * | 11/1981 | Sagae et al. | 604/44 |
| 4,314,565 A * | 2/1982 | Lee | 600/566 |
| 4,531,935 A * | 7/1985 | Berryessa | 604/45 |
| 4,619,643 A * | 10/1986 | Bai | 604/43 |
| 4,626,240 A * | 12/1986 | Edelman et al. | 604/43 |
| 4,767,407 A * | 8/1988 | Foran | 604/164.06 |
| 4,810,244 A * | 3/1989 | Allen | 604/44 |
| 4,850,373 A * | 7/1989 | Zatloukal et al. | 600/562 |
| 4,935,008 A * | 6/1990 | Lewis, Jr. | 604/510 |
| 4,994,047 A * | 2/1991 | Walker et al. | 604/264 |
| 5,156,596 A * | 10/1992 | Balbierz et al. | 604/164.11 |
| 5,160,319 A * | 11/1992 | Emery et al. | 604/27 |
| 5,250,038 A * | 10/1993 | Melker et al. | 604/264 |
| 5,373,855 A | 12/1994 | Skrabal et al. | |
| 5,735,813 A * | 4/1998 | Lewis | 604/43 |
| 5,843,023 A * | 12/1998 | Cecchi | 604/44 |
| 5,935,110 A * | 8/1999 | Brimhall | 604/167.06 |
| 6,506,181 B2 * | 1/2003 | Meng et al. | 604/164.07 |

FOREIGN PATENT DOCUMENTS

| | | |
|---|---|---|
| DE | 3522782 A1 | 1/1987 |
| DE | 3702441 A1 | 8/1988 |
| JP | 2001-190560 | 7/2001 |
| WO | WO 00/18464 | 4/2000 |
| WO | WO 00/53108 | 9/2000 |

* cited by examiner

Primary Examiner—Glenn K. Dawson
Assistant Examiner—Michael G. Mendoza
(74) Attorney, Agent, or Firm—Louis Woo

(57) ABSTRACT

The rear end of a dual lumen oocyte recovery needle is sealed in a plastics hub by means of two polyurethane seals compressed between the outside of the needle and opposite ends of a bore through the hub. The needle has an outer tube and an inner tube with a suction lumen along its length and which is deformed to provide a flushing lumen between its outside and the inside of the outer tube. A suction tube is joined to the rear end of the needle at the rear end of the hub in communication with the suction lumen. A flushing tube is joined in a side bore opening into the interior of the hub and communicating via a slot in the side of the needle with the flushing lumen.

12 Claims, 1 Drawing Sheet

MEDICO-SURGICAL INSTRUMENTS

BACKGROUND OF THE INVENTION

This invention relates to medico-surgical instruments.

The invention is more particularly, but not exclusively, concerned with dual-lumen oocyte needles.

Oocyte needles are used to extract one or more oocyte from women for use in assisted reproduction procedures. The patient end of the needle is inserted in the ovary and gentle suction is applied to the other end so that the oocyte is sucked along the needle into a suitable receptacle. Some oocyte needles are dual lumen, that is, they have a smaller lumen in addition to the main suction lumen along which an irrigating or flushing fluid can be supplied to facilitate oocyte collection. The needles are made of metal and the machine or proximal end is terminated with a hub, usually of a plastics material by which connection can be made to both the suction lumen and the irrigating lumen. Such dual-lumen needles are sold, for example, by Rocket Limited of Watford, England and by Cook IVF of Queensland, Australia. It is important that the passage through the needle and hub is atraumatic for the oocyte, that there is no risk of leakage and that the instrument is easy to use. There are other medico-surgical instruments having a dual-lumen tubular member terminated at one end by a hub by which connection can be made to both lumens.

BRIEF SUMMARY OF THE INVENTION

It is an object of the present invention to provide an alternative medico-surgical instrument.

According to the present invention there is provided a medico-surgical instrument having a tubular member with a first and second lumen extending along its length and a hub attached with the member towards one end, the hub including a first port in fluid connection with the first lumen, the second lumen opening at a second port of the instrument, and the hub including a housing having an opening towards one end through which the tubular member extends into the housing and an annular sealing member of a compressible material embracing the tubular member and inserted in the opening in compression between the housing and the tubular member to provide a seal between the housing and the tubular member.

The first port is preferably located on a side of the housing and the second port is preferably located axially of the opening at the one end. The tubular member may have an opening formed in its side in communication with the first lumen in the tubular member and opening to the first port. The tubular member may extend in the second opening towards an opposite end of the housing, the instrument having a second annular sealing member of a compressible material embracing the tubular member and inserted in compression between the housing and the tubular member to provide a seal between the housing and the tubular member. The instrument may include a flexible joint joined on the outside of the tubular member at one end, an end of the tube extending in a recess in the compressible member. The flexible tube is preferably of a resilient material that grips the tubular member more tightly as force is applied to pull the tube off the tubular member. The instrument may include a colour-coded sleeve extending along the flexible tube where the tube is joined with the tubular member. The tubular member is preferably of a metal. The tubular member may comprise an outer metal tube and an inner metal tube extending along the outer tube as a close fit, a bore through the inner tube providing the second lumen, the inner tube being deformed inwardly in a region extending along the length of the tube so as to provide a passage between the inside of the outer tube and the outside of the inner tube, and the passage providing the first lumen. The housing may be of a transparent plastics material. The or each sealing member may be of polyurethane. The first lumen is preferably for flushing liquid and the second lumen is preferably for suction of an oocyte.

A dual-lumen oocyte needle assembly according to the present invention, will now be described, by way of example, with reference to the accompanying drawings.

DETAILED DESCRIPTION OF THE PREFERRED EMBODIMENT

Figure 1:
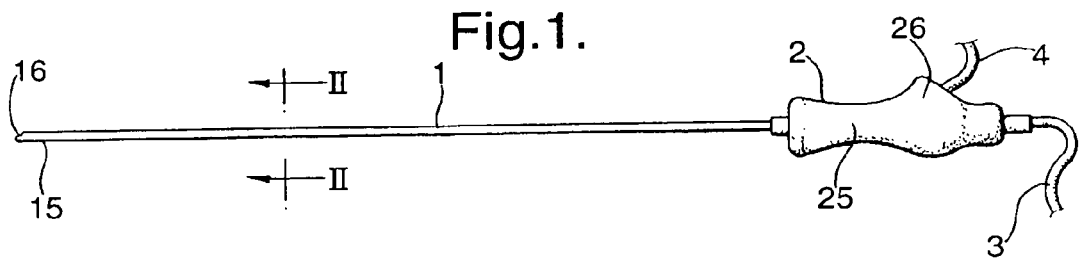
FIG. 1 is a side elevation view of the assembly.
Figure 2:
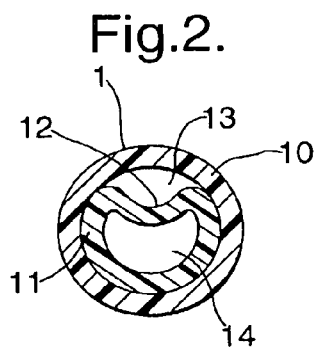
FIG. 2 is an enlarged transverse sectional view of the assembly along the line II—II of FIG. 1.
Figure 3:
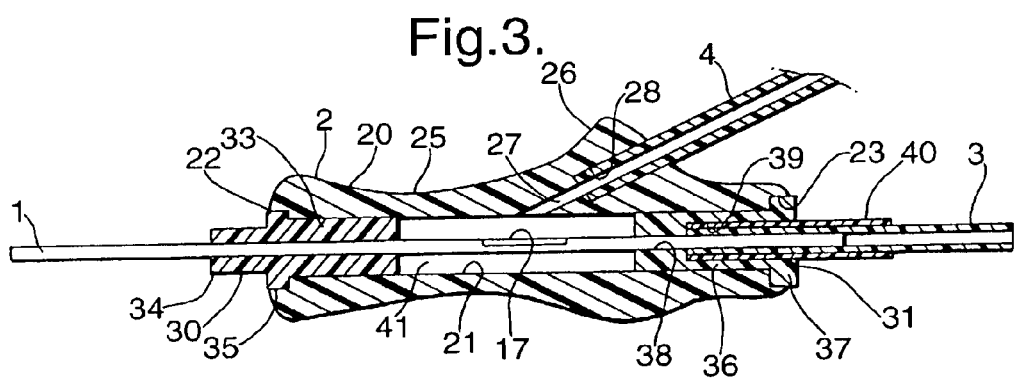
FIG. 3 is an enlarged cross-sectional view of the rear end of the assembly.

With reference first to FIGS. 1 to 3, the needle assembly comprises a rigid needle shaft 1 having a hub 2 at its rear or machine end and a suction tube 3 and flushing tube 4 attached with the hub.

The needle 1 is of a conventional dual-lumen construction. It comprises an outer tube 10 of stainless steel and an inner tube 11 of the same material which is a close, interference fit within the outer tube. The outer tube 10 has a circular section with an external diameter of 1.7 mm whereas the inner tube 11 is of circular section around the major part of its circumference but has an internally deformed section or groove 12 extending along its length. This section 12 forms a passage 13 between the outer and inner tubes 10 and 11, which provides the flushing lumen of the needle 1. The second, suction lumen is provided by the bore 14 through the inner tube 11.

The patient end 15 of the needle 1 is cut at a bevel 16 to permit penetration through tissue. A slot 17 is cut through the outer tube 10 in line with the flushing lumen 13 towards the rear end of the needle to provide communication with the flushing lumen. To the rear of the slot 17 the lumen 13 is closed by swaging out the deformed section 12 of the inner tube 11 so that it seals against the inside of the outer tube 10. This can be done by inserting a tapered pin within the rear end of the inner tube 11.

The hub 2 has an outer housing or body 20 moulded of a rigid, transparent plastics material such as a hard grade of polyurethane, for example, Tecoflex 65D. The body has an axial bore 21 extending along its length with short enlarged openings or recesses 22 and 23 at opposite ends. The external surface of the hub is profiled to enable gripping between the thumb and fingers of the user, having a waisted gripping portion 25. A fin 26 projects outwardly to the rear of the gripping portion on one side of the hub and a first port or flushing bore 27 extends through the fin at an angle of about 45° to the axis of the assembly. The flushing bore 27 opens into the axial bore 21 about midway along its length, the outer part 28 of the flushing bore being enlarged in diameter to receive the end of the flushing tube 4. The flushing tube 4 is of a softer grade of Tecoflex polyurethane than the body 20 and is secured in the outer part 28 of the bore 27 by means of a solvent applied to the outer surface of the tube.

The needle 1 extends axially through the hub 2 along the main bore 21 and projects from the hub at its rear end by about 5 mm. This provides a second port, which is axially aligned with the opening 22 at the forward end of the housing 20. The needle 1 is supported and sealed with the hub by means of two annular sealing members or stoppers 30 and 31. The stoppers 30 and 31 are both made of a soft grade of polyurethane, such as Tecoflex EG100A. The front stopper 30 is of circular section having an axial bore 32 extending along its length, the diameter of the bore being equal to the external diameter of the needle. Externally, the stopper 30 is divided into a rear part 33 and a forward part 34 by a radially projecting flange 35. The rear part 33 has a natural diameter, that is, before insertion in the body 20, slightly greater than the diameter of the bore 21. The flange 35 has a diameter closely matched with that of the recess 22. The forward part 34 is shorter than the rear part 37 and is of smaller diameter. The rear stopper 31 is of cylindrical shape with a forward end 36 and a radially-projecting flange 37 at its rear end. A bore 38 extends through the stopper 31, the forward part of which has a diameter equal to that of the needle 1. At its rear end, the bore 38 is enlarged to form a recess 39 that receives the suction tube 3 and a short, colour-coded sleeve 40 extending along the outside of the tube.

Figure 4:
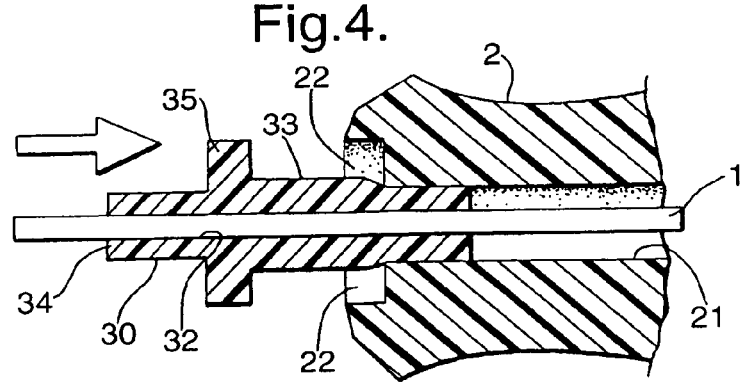
FIG. 4 is an enlarged cross-sectional view of a part of the rear end of the assembly at a preliminary stage of manufacture.

The hub 2 is assembled on the rear end of the needle 1 by first sliding the forward stopper 30 a short distance along the needle from its rear end and then inserting the rear end of the needle in the bore 21 of the body 20 so that its rear end projects by about 5 mm. A small amount of solvent is applied to the outside of the forward stopper 30, which is then slid rearwardly, as shown in FIG. 4, so that its rear end enters the bore 21. The solvent lubricates the stopper 30 as it enters the bore 21 and is compressed radially. The stopper 30 is inserted until the flange 35 locates in the recess 22. In this position, the rear part 33 of the stopper is compressed between the outside of the needle 1 and the inside of the hub body 20 so that a secure seal and mechanical grip is formed of the needle in the hub body. The solvent dries to lock the stopper 30 in the body 20. Similarly, a solvent is applied to the outside of the rear stopper 31 and this is slid forwardly into the rear end of the bore 21. When fully inserted, the stopper 31 is compressed between the needle 1 and the hub body 20 and is locked in position by the solvent. The suction tube 3 is then attached to the rear end of the needle 1 simply by pushing it onto the needle and into the enlarged rear end 39 of the bore 38 through the stopper 31. The suction tube 3 is of a relatively resilient material with a Poisson's ratio such that it provides a secure attachment to the needle 1 because any axial force applied to the tube tending to pull it off the needle has the effect of necking down the tube to apply a tighter gripping force to the needle. The internal diameter of the suction tube 3 and the length of needle 1 along which the tube extends are selected to produce a secure attachment. The sleeve 40 is slid into place within the rear end 39 of the stopper 31 so that about half its length projects rearwardly; it may be secured by a solvent. The sleeve 40 projects along the suction tube 3 a short distance beyond the end of the needle 1 so that, in addition to providing a colour-coding function, the sleeve may help prevent the suction tube bending sharply in the region of the rear end of the needle.

The two stoppers 30 and 31 block the ends of the bore 21 through the body 20 and form an internal cavity 41 into which open both the flushing bore 27 and the slot 17 in the needle 1. In this way, fluid connection is established between the flushing tube 4 and the flushing bore 13 in the needle 1.

The present invention overcomes the problem of how to provide a secure connection of a plastics hub on a metal needle. The construction is relatively simple and accommodates tolerances of the components. The hub can be made transparent so that any contamination, blockages or moulding defects are immediately obvious.

The invention is not confined to oocyte needle assemblies but could be used for other instruments where connection is needed to two bores extending along a tubular member.

What we claim is:

1. A medico-surgical instrument comprising: a dual-lumen tubular member, said dual-lumen tubular member having a first and second lumen extending along its length; and a hub attached with said dual-lumen tubular member towards one end, wherein said hub includes a housing, said housing including first and second ports and a bore extending along its length between opposite ends of said housing, wherein said dual-lumen tubular member extends into said housing from one end along said bore, wherein said first port is in fluid communication with said first lumen, wherein said second lumen opens at said second port, wherein said hub includes an elongate annular sealing member of a compressible material embracing said dual-lumen tubular member, and wherein the natural external diameter of the sealing member is greater than the diameter of said bore such that when the sealing member is inserted in said bore at said one end it is compressed between said housing and said dual-lumen tubular member to provide a seal between said housing and said tubular member, wherein said dual-lumen tubular member extends in a second opening towards an opposite end of said housing, and wherein said instrument has a second annular sealing member of a compressible material embracing said dual-lumen tubular member and inserted in compression between said housing and said dual-lumen tubular member to provide a seal between said housing and said dual-lumen tubular member.

2. An instrument according to claim 1, wherein said first port is located on a side of said housing.

3. An instrument according to claim 1, wherein said second port is located axially of said opening opposite said one end.

4. An instrument according to claim 1, wherein said dual-lumen tubular member has an opening formed in its side in communication with said first lumen and opening in fluid communication with said first port.

5. An instrument according to claim 1, wherein said dual-lumen tubular member is of metal.

6. An instrument according to claim 5, wherein said dual-lumen tubular member comprises an outer metal tube and an inner metal tube extending along said outer tube as a close fit, wherein a bore through said inner tube provides said second lumen, wherein said inner tube is deformed inwardly in a region extending along the length of said tube so as to provide a passage between an inside of said outer tube and an outside of said inner tube, and wherein said passage provides said first lumen.

7. An instrument according to claim 1, wherein said housing is of a transparent plastics material.

8. An instrument according to claim 1, wherein said sealing member is of a polyurethane.

9. A medico-surgical instrument comprising: a dual-lumen tubular member, said dual-lumen tubular member having a first and second lumen extending along its length; and a hub attached with said dual-lumen tubular member towards one end, wherein said hub includes a housing, said housing including first and second ports and a bore extending along its length between opposite ends of said housing, wherein said dual-lumen tubular member extends into said housing from one end along said bore, wherein said first port is in fluid communication with said first lumen, wherein said second lumen opens at said second port, wherein said hub includes an elongate annular sealing member of a compressible material embracing said dual-lumen tubular member, and wherein the natural external diameter of the sealing member is greater than the diameter of said bore such that when the sealing member is inserted in said bore at said one end it is compressed between said housing and said dual-lumen tubular member to provide a seal between said housing and said tubular member, wherein said instrument includes a flexible tube joined on an outside of said dual-lumen tubular member at said second port, and wherein an end of said tube extends in a recess in said compressible member.

10. An instrument according to claim 9, wherein said flexible tube is of a resilient material that grips said dual-lumen tubular member more tightly as force is applied to pull said tube off said tubular member.

11. An instrument according to claim 9 including a colour-coded sleeve extending along said flexible tube where said tube is joined with said dual-lumen tubular member.

12. A dual-lumen oocyte needle assembly comprising: a rigid needle having first and second lumens extending along its length; and a hub mounted at a rear end of said needle, said hub including a housing having a bore extending along its length and a side port opening into said bore, wherein said needle is sealed with said housing at opposite ends by means of two elongate stoppers of compressible material at each end of the housing, the natural external diameter of the stoppers being greater the diameter of that when the stoppers are inserted in said bore are compressed between the outside of the needle and the bore of said housing to make a sealing contact between the outside of the needle and the housing, wherein said first lumen opens through a side port between opposite ends of said housing, and wherein said second lumen opens at a rear end of said housing.

* * * * *